March 25, 1947. C. A. GREINER Plant Pat. 728
PEAR TREE
Filed Oct. 24, 1944
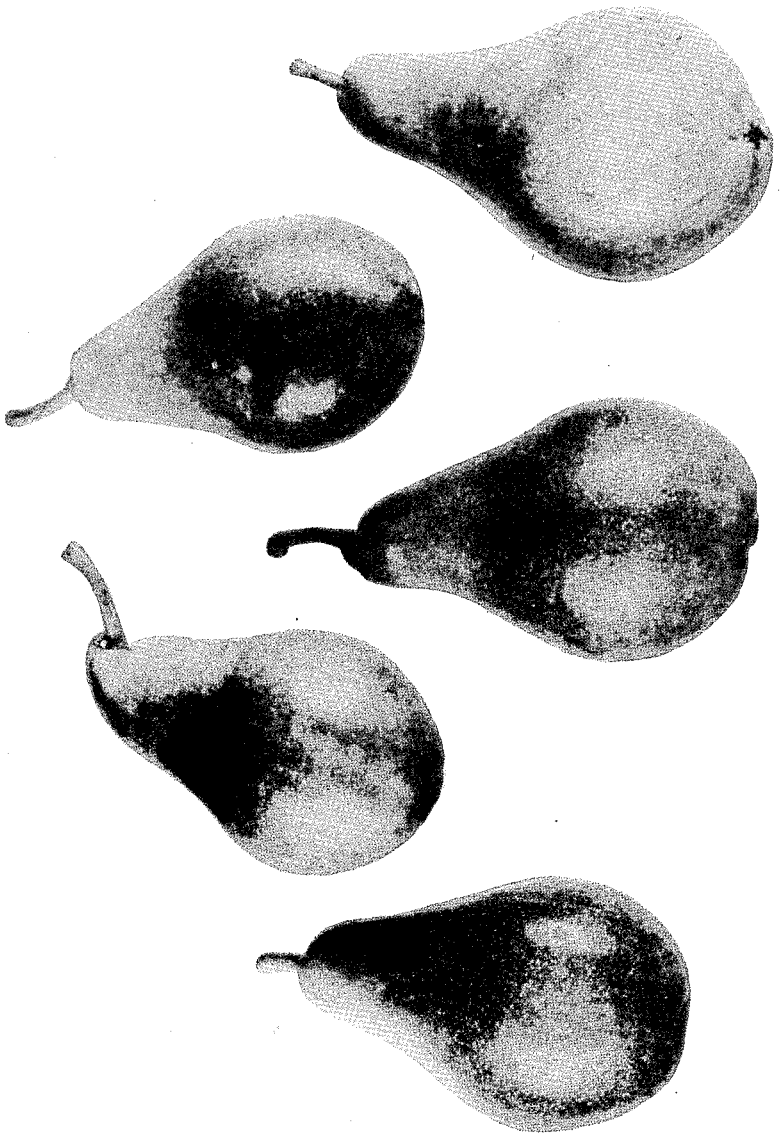
Inventor
C. A. Greiner
By Robbins Robb
His Attorneys Patented Mar. 25, 1947 Plant Pat. 728

UNITED STATES PATENT OFFICE

728

PEAR TREE

Charles A. Greiner, Marlboro, N. Y.

Application October 24, 1944, Serial No. 560,121

1 Claim. (Cl. 47—62)

The present discovery relates to a new and distinct variety of pear tree, originating as a chance seedling, that I found to have important characteristics distinguishing it from other known commercial varieties. These characteristics appear to be a combination of all the good qualities of both the "Bosc" and "Clapp's Favorite," and this new variety might well be presumed to be the progeny of these well known pears. However, the parentage is not known aside from this presumption.

One of the most important features of novelty of this new pear is its resistance to blight and to the devastating action of pear psylla. This was observed by me, speaking with reference to the original seedling, which was grown among a group of Seckel, Bosc, and Clapp's Favorite trees, when the seedling showed no psylla injury while the surrounding varieties lost most of their foliage due to psylla.

The applicant has grafted 100 trees by top working, and has root grafted about 200 seedlings, to reproduce asexually this variety. From observation over a period of three years, said trees and progeny have been and are free of pear psylla and fire blight, although other pear varieties in the same orchard have been afflicted with these diseases.

The new variety is much more vigorous than any variety I have ever seen. It is also as productive as Clapp's Favorite, but somewhat larger in size and longer in shape, resembling the Bosc variety in this respect, but in color it is more nearly like Clapp's Favorite.

Top working of this variety shows that the characteristics referred to and disclosed more in detail hereinafter are established and come true to form.

The accompanying illustration shows a number of specimens of this new variety taken about two weeks before maturity and arranged in different positions to illustrate their uniformity and other physical characteristics as nearly as these can be presented by illustration.

The following is a detailed description of the new variety, color terminology according with ordinary dictionary definition.

(Observations set forth made on specimens grown on farm in Marlboro, New York.)

Dates first and last picking: September 1st–September 10th.

*Tree*

Large; very vigorous; upright; tall; vase-formed; rapid growing; hardy; very productive; alternate year heavy bearing.

Trunk: Stocky; medium smooth.

Branches: Medium thick; medium smooth; branching short laterals.

*New growth.*—Red.

*Old growth.*—Grey.

*Lenticels.*—Medium number; medium size.

Leaves: Length—2½ to 3 inches. Width—1⅛ to 1½ inches. Medium size; medium width; medium length; ovate; taper-pointed; medium thick; Dark Green; smooth.

*Margin.*—Finely serrate.

*Petiole.*—Length—1½ to 2½ inches; average 1½ to 2 inches. Long; medium thick.

Flowers: Date of first bloom—about May 5th. Date of full bloom—about May 10th to 12th. Medium early; small; white.

Fruit: Maturity when described—hard.

*Size.*—Uniform. Axial diameter—2¼ to 2½ inches; transverse—4 to 4½ inches.

*Form.*—Oblong; conical; long tapering neck; very smooth and regular.

*Cavity.*—Lacking.

*Basin.*—Symmetrical; rounded; narrow; furrowed slightly; glabrous. Depth—$\frac{1}{16}$ to ⅛ inch. Breadth—⅜ to ½ inch. Markings—none.

*Stem.*—Clubbed; medium slender; glabrous. Length—1 to 1½ inches. Breadth—⅛ to ¼ inch. Markings—few lenticels; color, Green with Brown washing.

*Calyx.*—Open to closed; segments persistent; acute. Length—$\frac{3}{16}$ inch. Prostrate; converged from base toward center. Outer and inner surfaces—glabrous.

*Eye.*—Medium size; open.

*Skin.*—Medium glossy; slightly oily. Dots—conspicuous; many; even; circular; color—greenish; distribution—general. Ground color—Green to Yellow Green. Color markings—Red cheek; striped on neck; marbled. Bloom—moderate. Scarfskin—wanting. General color effect—Green, Red cheek.

Flesh: Juicy.

*Color of flesh.*—White with yellowish-greenish tint.

*Texture.*—Firm; tender; fine; melting.

*Flavor.*—Mild; sweet.

*Quality.*—Good to best.

Core: Median.

*Bundle area.*—Very small; cordate; symmetrical.

*Halves of area.*—Equal.

*Bundles.*—Green; two whorls.

*Alternate bundle.*—Reaches tube below stamens.

3

*Core lines.*—Meeting. In cross section—indistinct.

*Carpellary area.*—Indistinct; small.

*Calyx tube.*—Almost wanting; urn-shaped. Stem of funnel—very short. Depth of tube to shoulder—$1\frac{1}{16}$ to ⅛ inch. Styles—wanting.

*Stamens.*—Marginal.

*Axillary cavity.*—Wanting.

*Seed cells.*—Axile; closed. Cell walls—very thin; tender. Length, $\frac{9}{16}$ inch; breadth, $\frac{5}{16}$ inch. Longitudinal section — obcordate. Surface—smooth. Cross section—narrow.

Seeds:

*Number perfect.*—Eight.

*Number imperfect.*—Three to four.

4

*Largest number.*—Eight.

*Number in one cell.*—None to two. Length, ½ inch; breadth, ¼ inch.

*Form.*—Acuminate.

*Color.*—Light to Dark Brown.

Use: Market.

Keeping quality: Good. Number of days in ordinary storage, 20.

Resistance to: Insects and diseases—good.

I claim:

A new and distinct variety of pear tree, characterized predominately as to novelty by its great vigor, its resistance to blight and pear psylla, and the uniformity, marking and shape of the fruit thereof, substantially as shown and described.

CHARLES A. GREINER.